(12) United States Patent
Jester et al.

(10) Patent No.: US 10,292,865 B2
(45) Date of Patent: *May 21, 2019

(54) NONLINEAR OPTICAL PHOTODYNAMIC THERAPY (NLO-PDT) OF THE CORNEA

(71) Applicant: The Regents of the University of California, Oakland, CA (US)

(72) Inventors: James V. Jester, Irvine, CA (US); Tibor Juhasz, Corona del Mar, CA (US); Donald J. Brown, Santa Clarita, CA (US); Dongyul Chai, Costa Mesa, CA (US); Moritz Winkler, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/803,451

(22) Filed: Jul. 20, 2015

(65) Prior Publication Data

US 2015/0320599 A1    Nov. 12, 2015

Related U.S. Application Data

(60) Division of application No. 13/919,547, filed on Jun. 17, 2013, now Pat. No. 9,095,414, which is a
(Continued)

(51) Int. Cl.
*A61F 9/008*    (2006.01)
*A61F 9/01*    (2006.01)
*A61N 5/06*    (2006.01)

(52) U.S. Cl.
CPC .......... *A61F 9/00802* (2013.01); *A61F 9/008* (2013.01); *A61F 9/00804* (2013.01);
(Continued)

(58) Field of Classification Search
None
See application file for complete search history.

(56) References Cited

U.S. PATENT DOCUMENTS 5,984,916 A    11/1999   Lai
6,042,603 A     3/2000   Fisher et al.
(Continued)

OTHER PUBLICATIONS

David E. Wolf, Sensor Technologies LLC, What is the Confocal Volume?, Sep. 15, 2008, retrieved with the wayback machine with link: http://www.fcsxpert.com/classroom/theory/what-is-confocal-volume.html.*

(Continued)

*Primary Examiner* — Carl H Layno
*Assistant Examiner* — Manolis Pahakis
(74) *Attorney, Agent, or Firm* — Knobbe, Martens, Olson & Bear LLP

(57) ABSTRACT

The embodiments include method of nonlinear optical photodynamic therapy of tissue including the steps of providing pulsed infrared laser light for two-photon excited fluorescence tissue exposure, and selectively focusing the pulsed infrared laser light within the tissue at a focal plane to activate a photosensitizing agent to generate free radicals within a highly resolved axial and lateral spatial domain in the tissue. The invention is also directed to an apparatus for performing nonlinear optical photodynamic therapy of tissue including a pulsed infrared laser for providing two-photon excited fluorescence beam tissue exposure, a scanner for selectively and controllably moving the tissue and the beam relative to each other, and optics for selectively focusing the pulsed infrared laser light within the tissue at a point in a focal plane to activate a photosensitizing agent to generate free radicals within a highly resolved axial and lateral spatial domain in the tissue.

15 Claims, 12 Drawing Sheets

Related U.S. Application Data continuation-in-part of application No. 13/523,058, filed on Jun. 14, 2012, now abandoned.

(60) Provisional application No. 61/500,801, filed on Jun. 24, 2011.

(52) U.S. Cl.
CPC .......... *A61F 9/00825* (2013.01); *A61N 5/062* (2013.01); *A61F 2009/00872* (2013.01); *A61F 2009/00893* (2013.01); *A61F 2009/00895* (2013.01)

(56) References Cited

U.S. PATENT DOCUMENTS

| | | | |
|---|---|---|---|
| 6,325,792 B1 | 12/2001 | Swinger et al. | |
| 6,370,422 B1* | 4/2002 | Richards-Kortum | A61B 5/0068 |
| | | | 600/182 |
| 6,750,968 B2 | 6/2004 | Sandusky | |
| 6,751,033 B2 | 6/2004 | Goldstein et al. | |
| 6,791,060 B2 | 9/2004 | Dunsky et al. | |
| 6,997,923 B2 | 2/2006 | Anderson et al. | |
| 7,053,991 B2 | 5/2006 | Sandusky | |
| 7,142,312 B2 | 11/2006 | Quadling et al. | |
| 7,245,412 B2 | 7/2007 | Bruland et al. | |
| 7,342,219 B2 | 3/2008 | Araya et al. | |
| 7,353,829 B1 | 4/2008 | Wachter et al. | |
| 7,468,837 B2 | 12/2008 | Brooker | |
| 7,615,721 B2 | 11/2009 | Fukuyo et al. | |
| 7,626,137 B2 | 12/2009 | Fukuyo et al. | |
| 7,732,730 B2 | 6/2010 | Fukuyo et al. | |
| 7,736,382 B2 | 6/2010 | Webb et al. | |
| 7,825,350 B2 | 11/2010 | Fukuyo et al. | |
| 7,898,925 B2 | 3/2011 | Shiono et al. | |
| 7,902,526 B2 | 3/2011 | Kim et al. | |
| 7,943,384 B2 | 5/2011 | Durack et al. | |
| 7,982,169 B2 | 7/2011 | Kittelmann et al. | |
| 8,054,542 B2 | 11/2011 | Sasaki et al. | |
| 8,218,840 B2 | 7/2012 | Eisfeld et al. | |
| 8,227,724 B2 | 7/2012 | Fukuyo et al. | |
| 8,262,647 B2 | 9/2012 | Raksi et al. | |
| 8,267,925 B2 | 9/2012 | Raksi et al. | |
| 8,419,721 B2 | 4/2013 | Raksi et al. | |
| 8,425,496 B2 | 4/2013 | Vogler | |
| 8,425,499 B2 | 4/2013 | Donitzky et al. | |
| 8,441,633 B2 | 5/2013 | Truong et al. | |
| 8,506,559 B2 | 8/2013 | Raksi | |
| 8,969,761 B2 | 3/2015 | Fukuyo et al. | |
| 2004/0002199 A1 | 1/2004 | Fukuyo et al. | |
| 2004/0199149 A1* | 10/2004 | Myers | A61F 9/008 |
| | | | 606/4 |
| 2004/0243111 A1 | 12/2004 | Bendett et al. | |
| 2005/0107773 A1 | 5/2005 | Bergt et al. | |
| 2005/0173387 A1 | 8/2005 | Fukuyo et al. | |
| 2005/0181581 A1 | 8/2005 | Fukuyo et al. | |
| 2005/0224469 A1 | 10/2005 | Cutler et al. | |
| 2006/0020309 A1 | 1/2006 | Altshuler et al. | |
| 2006/0087727 A1 | 4/2006 | Brooker | |
| 2006/0093265 A1* | 5/2006 | Jia | B23K 26/03 |
| | | | 385/37 |
| 2006/0095097 A1 | 5/2006 | Dees et al. | |
| 2006/0095101 A1 | 5/2006 | Dees et al. | |
| 2006/0114948 A1 | 6/2006 | Lo et al. | |
| 2006/0195076 A1* | 8/2006 | Blumenkranz | A61F 9/00736 |
| | | | 606/4 |
| 2006/0235370 A1* | 10/2006 | Oblong | A61B 18/203 |
| | | | 606/9 |
| 2007/0010803 A1 | 1/2007 | Bischoff et al. | |
| 2007/0010804 A1 | 1/2007 | Rathjen et al. | |
| 2007/0057211 A1 | 3/2007 | Bahlman et al. | |
| 2007/0123845 A1 | 5/2007 | Lubatschowski | |
| 2007/0173795 A1 | 7/2007 | Frey et al. | |
| 2008/0081950 A1* | 4/2008 | Koenig | A61B 1/00172 |
| | | | 600/160 |
| 2008/0130458 A1 | 6/2008 | Shiono et al. | |
| 2008/0186551 A1 | 8/2008 | Hanft et al. | |
| 2008/0228178 A1 | 9/2008 | Van Hal et al. | |
| 2008/0281303 A1 | 11/2008 | Culbertson et al. | |
| 2008/0319428 A1 | 12/2008 | Wiechmann et al. | |
| 2008/0319464 A1 | 12/2008 | Bischoff et al. | |
| 2009/0012507 A1 | 1/2009 | Culbertson et al. | |
| 2009/0028407 A1* | 1/2009 | Seibel | A61B 1/0008 |
| | | | 382/131 |
| 2009/0036880 A1 | 2/2009 | Bischoff et al. | |
| 2009/0109527 A1 | 4/2009 | Sasaki et al. | |
| 2009/0247997 A1 | 10/2009 | Watanabe et al. | |
| 2009/0247999 A1 | 10/2009 | Tuan et al. | |
| 2009/0275929 A1 | 11/2009 | Zickler | |
| 2009/0278058 A1 | 11/2009 | Kim et al. | |
| 2010/0016783 A1* | 1/2010 | Bourke, Jr. | A61K 41/0057 |
| | | | 604/20 |
| 2010/0025387 A1 | 2/2010 | Arai et al. | |
| 2010/0049175 A1 | 2/2010 | Rathjen et al. | |
| 2010/0082018 A1* | 4/2010 | Panthakey | A61F 9/0079 |
| | | | 606/5 |
| 2010/0137982 A1 | 6/2010 | Culbertson et al. | |
| 2010/0176100 A1 | 7/2010 | Fukuyo et al. | |
| 2010/0191226 A1 | 7/2010 | Blumenkranz et al. | |
| 2010/0270479 A1 | 10/2010 | Webb et al. | |
| 2010/0316959 A1 | 12/2010 | Gates et al. | |
| 2010/0318073 A1 | 12/2010 | Vogler et al. | |
| 2010/0331831 A1 | 12/2010 | Bischoff et al. | |
| 2011/0028948 A1 | 2/2011 | Raksi et al. | |
| 2011/0028949 A1 | 2/2011 | Raksi et al. | |
| 2011/0028950 A1 | 2/2011 | Raksi et al. | |
| 2011/0028951 A1 | 2/2011 | Raksi et al. | |
| 2011/0028952 A1 | 2/2011 | Raksi et al. | |
| 2011/0028957 A1 | 2/2011 | Raksi | |
| 2011/0122488 A1 | 5/2011 | Truong et al. | |
| 2011/0132885 A1 | 6/2011 | Sercel et al. | |
| 2011/0134521 A1 | 6/2011 | Truong et al. | |
| 2011/0202046 A1 | 8/2011 | Angeley et al. | |
| 2011/0237999 A1* | 9/2011 | Muller | A61F 9/008 |
| | | | 604/20 |
| 2012/0049087 A1 | 3/2012 | Choi et al. | |
| 2012/0215155 A1* | 8/2012 | Muller | A61F 9/0079 |
| | | | 604/20 |
| 2012/0234807 A1* | 9/2012 | Sercel | B23K 26/0608 |
| | | | 219/121.69 |
| 2012/0271286 A1 | 10/2012 | Curatu et al. | |
| 2012/0303008 A1* | 11/2012 | Muller | A61F 9/013 |
| | | | 606/5 |
| 2012/0310223 A1 | 12/2012 | Knox et al. | |
| 2012/0316544 A1* | 12/2012 | Horvath | A61F 9/00825 |
| | | | 606/6 |
| 2013/0110091 A1* | 5/2013 | Berry | A61N 5/062 |
| | | | 606/3 |
| 2013/0338650 A1* | 12/2013 | Jester | A61F 9/00804 |
| | | | 606/5 |
| 2014/0194860 A1* | 7/2014 | Dick | A61F 9/00825 |
| | | | 606/6 |
| 2014/0257259 A1* | 9/2014 | Papastathopoulos | |
| | | | A61F 9/00825 |
| | | | 606/4 |
| 2015/0051497 A1* | 2/2015 | Carver | A61B 5/0071 |
| | | | 600/476 |
| 2016/0003742 A1* | 1/2016 | Butte | G01N 21/6408 |
| | | | 250/459.1 |
| 2017/0252858 A1* | 9/2017 | Zediker | B23K 26/0622 |
| 2018/0311508 A1* | 11/2018 | Ellingwood | A61M 5/178 |

OTHER PUBLICATIONS

Zipfel et al., Nonlinear magic: multiphoton microscopy in the biosciences, Nature Biotechnology vol. 21 No. 11 Nov. 2003.*

Denk, et al. 1990 "Two-photon laser scanning fluorescence microscopy" *New Series* 248(4951): 73-76.

(56) References Cited

OTHER PUBLICATIONS

Dong et al. 2011 "Collagen Cross-Linking With Riboflavin in a Femtosecond Laser-Created Pocket in Rabbit Corneas: 6-Month Results" *Am J Ophthalmol* 152: 22-27.

Ji, et al. 2008 "Advances in the speed and resolution of light microscopy" *Current Opinion in Neurobiology* 18: 605-616.

Kanellopoulos 2009 "Collagen Cross-linking in Early Keratoconus With Ribofl avin in a Femtosecond Laser-created Pocket: Initial Clinical Results" *J Refract Surg* 25: 1034-1037.

Kim et al. 2012 "Ray-tracing study of the post-scanner variable beam expansion optics in a two-photon microscopy system" *Multiphoton Microscopy in the Biomedical Sciences XII* 8226: pp. 1-9.

Kuetemeyer, et al. 2011 "Two-photon induced collagen cross-linking in bioartificial cardiac tissue" *Optics Express* 19(17): 15996-16007.

Lafratta, et al. 2007 "Multiphoton Fabrication" *Angew. Chem. Int. Ed.* 46: 6238-6258.

Maxwell, et al. 2006 "Application of femtosecond lasers for subcellular nanosurgery" *Thesis, Harvard University*: pp. 1-149.

Oron, et al. 2012 "Two-photon optogenetics" *Progress in Brain Research* 196: 119-143.

Raiskup et al. 2013 "Corneal Crosslinking with Riboflavin and Ultraviolet A. I. Principles" *The Ocular Surface* 11: 65-74.

Reddy, et al. 2013 "High-speed two-photon imaging" *Cold Spring Harb Protoc*: pp. 1-7.

Rickgauer, et al. 2009 "Two-photon excitation of channelrhodopsin-2 at saturation" *Proceedings of the National Academy of Sciences* 106(35): 15025-15030.

Wollensak et al. 2013 "Biomechanical Efficacy of Collagen Crosslinking in Porcine Cornea Using a Femtosecond Laser Pocket" *Cornea* 33: 300-305.

Zhang et al. 2011 "Collagen Cross-Linking with Riboflavin in a Femtosecond Laser-Created Pocket in Rabbit Corneas" *Am J Ophthalmol* 152: 1082-1083.

\* cited by examiner

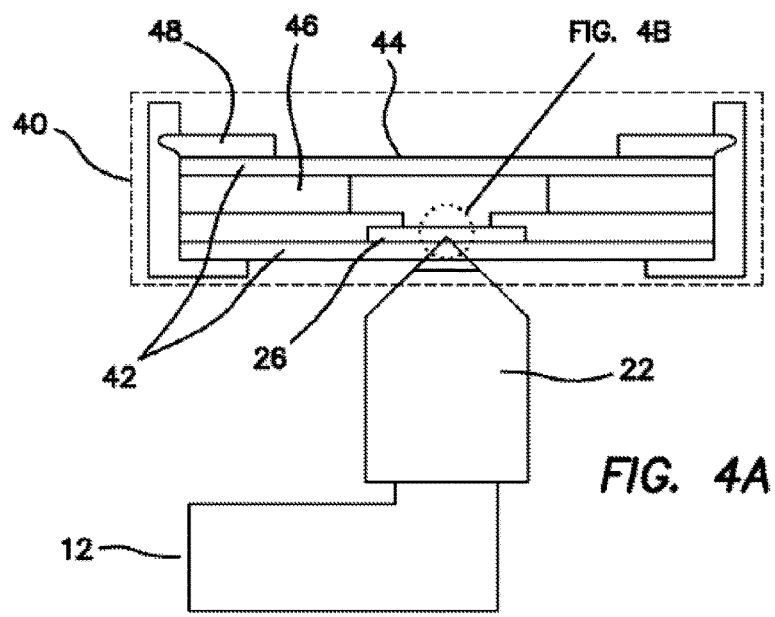
FIG. 4A
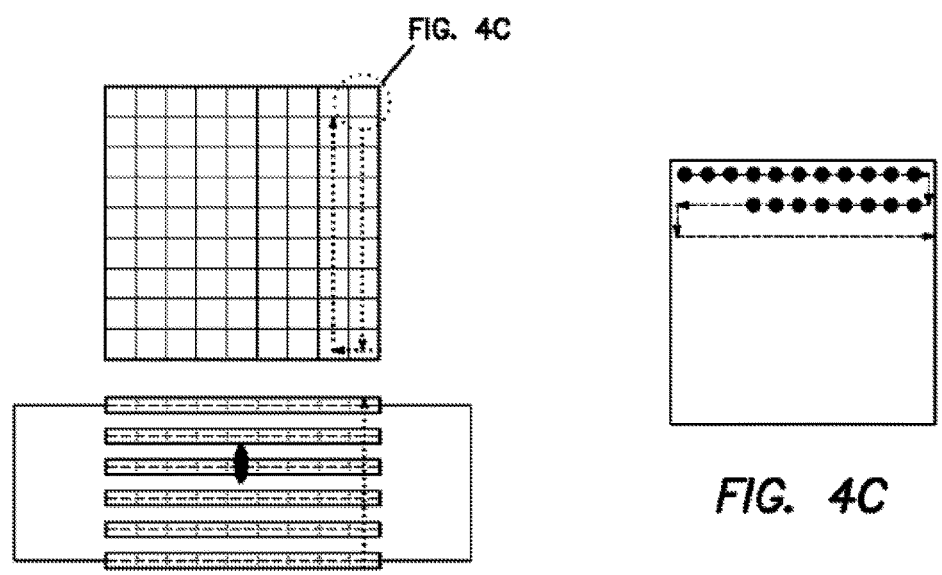
FIG. 4B
FIG. 4C

NONLINEAR OPTICAL PHOTODYNAMIC THERAPY (NLO-PDT) OF THE CORNEA

RELATED APPLICATIONS

The present application is a divisional of U.S. application Ser. No. 13/919,547, filed Jun. 17, 2013, issued as U.S. Pat. No. 9,095,414 on Aug. 4, 2015, which is a continuation in part of U.S. application Ser. No. 13/523,058, now abandoned, filed on Jun. 14, 2012, which in turn was related to U.S. Provisional Patent Application Ser. No. 61/500,801, filed on Jun. 24, 2011, all of which are incorporated herein by reference and to which priority is claimed pursuant to 35 U.S.C. § 119.

STATEMENT REGARDING FEDERALLY SPONSORED R&D

This invention was made with government support under EY007348 and EY018655, awarded by The National Eye Institute of the National Institutes of Health. The government has certain rights in the invention.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The disclosure relates to the field of using nonlinear optical photodynamic therapy (NLO-PDT) to cause collagen crosslinking using infrared light and riboflavin in the cornea.

Description of the Related Art

Numerous reports in the scientific literature relate to corneal collagen crosslinking, but none relate to the use of femtosecond lasers to activate photosensitizers in the cornea. Several recent papers report evaluation of collagen crosslinking following femtosecond laser generated tunnels in the cornea, but the researchers did not use the laser to activate a photosensitizer. In the past, crosslinking in the cornea has used UV light to activate the photosensitizer, riboflavin. The disadvantage of this approach is that it uses nonfocused light, which broadly and nonspecifically generates free radicals throughout the tissue volume, wherever the light penetrates.

SUMMARY OF THE INVENTION

The illustrated embodiments of the invention are directed to apparatus and methods of using nonlinear optical (NLO), femtosecond-near infrared lasers used to activate photosensitizing chemicals in the cornea for various corneal treatments including corneal stiffening to treat corneal ectasia, refractive errors and astigmatism as well as provide antimicrobial and tumorcidal effects.

In particular the illustrated embodiments are directed to a method of nonlinear optical photodynamic therapy of tissue including the steps of providing pulsed infrared laser light for multiphoton tissue exposure, and selectively focusing the pulsed infrared laser light within the tissue at a focal plane to activate a photosensitizing agent to generate free radicals within a highly resolved axial and lateral spatial domain in the tissue.

The method may further include the step of pretreating the tissue with the photosensitive agent prior to selectively focusing the pulsed infrared laser light within the tissue. The photosensitive agent includes but not limited to riboflavin.

The step of providing pulsed infrared laser light includes providing near-infrared light to minimize cellular damage by reducing photon energy level of the laser light and increasing depth penetration into the tissue.

In the embodiment where the tissue is a cornea the step of selectively focusing the pulsed infrared laser light within the tissue includes providing sufficient intensity and length of irradiation to cause collagen crosslinking (CXL) effective for corneal stiffening.

In the embodiment where the tissue is a cornea the step of selectively focusing the pulsed infrared laser light within the tissue includes providing sufficient intensity and length of irradiation to effectively provide anti-microbial mediation to treat a corneal infection.

In the embodiment where the tissue is a cornea the step of selectively focusing the pulsed infrared laser light within the tissue includes providing sufficient intensity and length of irradiation to effectively inhibit corneal swelling in bullous keratopathy.

In the embodiment where the tissue is a cornea the step of selectively focusing the pulsed infrared laser light within the tissue includes providing sufficient intensity and length of irradiation to effectively kill cells, bacteria, tumors or neovascular vessels growing into the avascular cornea.

In one embodiment the step of selectively focusing the pulsed infrared laser light within the tissue includes providing sufficient intensity and length of irradiation to effectively activate the photosensitizing agent only at the focal plane.

In the embodiment where the tissue is a cornea the step of selectively focusing the pulsed infrared laser light within the tissue includes providing sufficient intensity and length of irradiation to effectively cause corneal stiffening by collagen crosslinking to precisely stiffen weakened corneas, including keratoconus and post-LASIK ectasia.

In the embodiment where the tissue is a cornea the step of selectively focusing the pulsed infrared laser light within the tissue includes providing sufficient intensity and length of irradiation to effectively cause corneal stiffening, flattening and steepening to precisely stiffen, flatten and steepen regions of the cornea to treat astigmatism and refractive errors associated with myopia, hyperopia and presbyopia.

In the embodiment where the tissue is a cornea the step of selectively focusing the pulsed infrared laser light within the tissue includes providing sufficient intensity and length of irradiation to effectively treat bacterial, fungal, and amoebic infections of the eye without antibiotics.

In the embodiment where the tissue is a cornea the step of selectively focusing the pulsed infrared laser light within the tissue includes providing sufficient intensity and length of irradiation to effectively kill labeled tumor cells in the eye following loading with photosensitizing dyes.

In the embodiment where the tissue is a cornea the step of selectively focusing the pulsed infrared laser light within the tissue includes providing sufficient intensity and length of irradiation to effectively treat clinical diseases including keratoconus, post-LASIK ectasia, astigmatism, myopia, hyperopia, infection and ocular tumors.

The embodiments of the invention also include an apparatus for performing nonlinear optical photodynamic therapy of tissue including a pulsed infrared laser for providing multiphoton tissue exposure, a scanner for selectively and controllably moving the tissue and the beam relative to each other, and optics for selectively focusing the pulsed infrared laser light within the tissue at a point in a focal plane to activate a photosensitizing agent to generate free radicals within a highly resolved axial and lateral spatial domain in the tissue.

The pulsed infrared laser light includes a near-infrared laser to minimize cellular damage by reducing energy level of the laser light and increasing depth penetration into the tissue.

In the embodiment where the tissue is a cornea the pulsed infrared laser is arranged and configured with the optics to provide sufficient intensity and length of irradiation to cause collagen crosslinking (CXL) effective for corneal stiffening, selective activation of anti-microbial medication to treat a corneal infection, inhibition of corneal swelling in bullous keratopathy, or selective killing of cells, bacteria, tumors or neovascular vessels growing into the avascular cornea.

In the embodiment where the tissue is a cornea the selectively focused pulsed infrared laser is arranged and configured with the optics to provide sufficient intensity and length of irradiation to effectively cause corneal stiffening by collagen crosslinking to precisely stiffen weakened corneas, including keratoconus and post-LASIK ectasia.

In the embodiment where the tissue is a cornea the selectively focused pulsed infrared laser is arranged and configured with the optics to provide sufficient intensity and length of irradiation to effectively cause corneal stiffening and flattening to precisely stiffen and flatten regions of the cornea to treat astigmatism and refractive errors associated with myopia, hyperopia and presbyopia.

In the embodiment where the tissue is a cornea the selectively focused pulsed infrared laser is arranged and configured with the optics to provide sufficient intensity and length of irradiation to effectively treat bacterial, fungal, and amoebic infections of the eye without antibiotics, or to effectively kill labeled tumor cells in the eye following loading with photosensitizing dyes.

In another embodiment the invention is a method of nonlinear optical photodynamic therapy of tissue including the steps of providing a focal spot of a pulsed infrared laser light for multiphoton tissue exposure through a focusing lens. The focal spot has a volume and the focusing lens has an effective numerical aperture. The focal spot is selectively, repetitively and three dimensionally positioned in the tissue in a selected volume of the tissue, which is larger than the volume of the focal spot, to expose the selected volume of tissue to the pulsed infrared laser light within a predetermined clinical time span. The focal spot is provided with a selected focal volume and predetermined safe intensity sufficient to activate a photosensitizing agent in the tissue in the volume of tissue to generate free radicals within a highly resolved axial and lateral spatial domain in the tissue by utilizing the predetermined safe intensity of the focal spot and by adjusting the volume of the focal spot of the pulsed infrared laser light by variably adjusting the effective numerical aperture of the focusing lens.

Another embodiment is characterized as an apparatus for performing nonlinear optical photodynamic therapy of tissue including a pulsed infrared laser for providing a beam for multiphoton tissue exposure having a beam width at a predetermined safe intensity. The beam position is controlled by a scanner, which selectively and controllably moves the tissue and the beam relative to each other in an x and y plane. The scanned beam is modified by a variable beam expander for selectively varying the beam width or diameter. A focusing lens focuses the beam at a depth in the tissue with a selected focal volume and is selectively movable relative to the tissue along a z axis perpendicular to the x and y plane in order to selectively position the depth of the beam in the tissue. Adjustment of the beam expander selectively adjusts the effective numerical aperture of the focusing lens and hence the focal volume of the beam in the tissue. The focusing lens selectively focuses the pulsed infrared laser light within the tissue at a point in a focal plane to activate a photosensitizing agent to generate free radicals within a highly resolved axial and lateral spatial domain in the tissue.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

FIGS. 4a-4c are diagrammatic depictions of the apparatus and the scanning pattern by which the gels are irradiated using nonlinear optical photodynamics with a pulsed infrared laser light for two-photon excited fluorescence.

DETAILED DESCRIPTION OF THE PREFERRED EMBODIMENT

Figure 1:
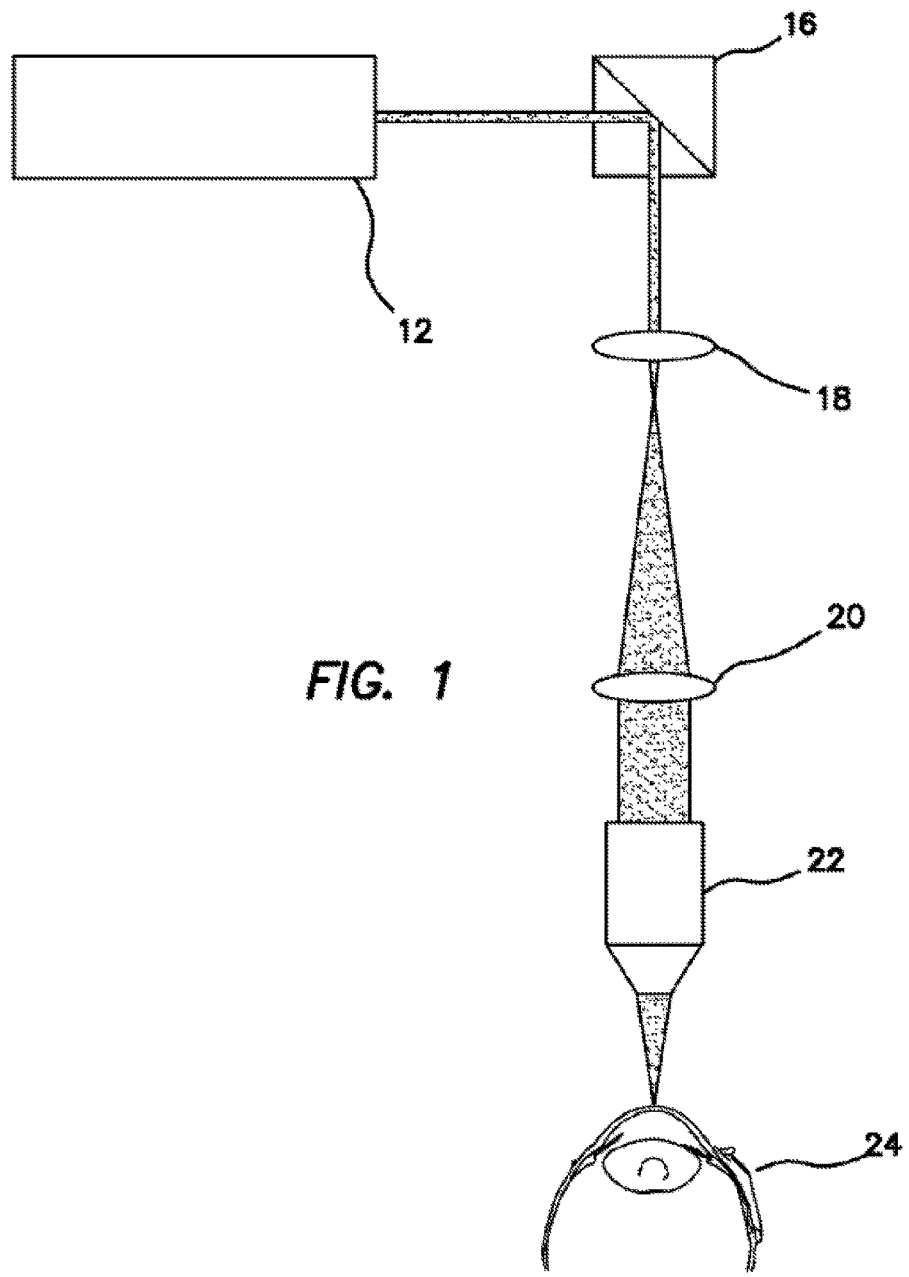
FIG. 1 is a schematic diagram of an apparatus in which the invention may be practiced or embodied.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

It is known that collagen crosslinking can be caused using UV light and riboflavin in the cornea and that there is a correlation between collagen autofluorescence induced by crosslinking and the mechanical stiffening effects of UV-riboflavin. Autofluorescence is the natural emission of light by biological structures, such as mitochondria and lysosomes, when they have absorbed light, and is used to distinguish the light originating from artificially added fluorescent markers (fluorophores). We have established that collagen autofluorescence can be used to evaluate collagen crosslinking and that the intensity of autofluorescence is correlated with the amount of corneal stiffening. We have further developed preliminary data showing the NLO-PDT can induce increased corneal stromal autofluorescence in riboflavin soaked corneas. We also have data showing that NLO-PDT increases collagen gel stiffness, showing the proof of concept.

NLO-PDT uses very short pulsed laser light that can be accurately focused within tissues to activate photosensitizing chemicals such as riboflavin to generate free radicals within highly resolved spatial domains, axially and laterally. The very short-pulsed laser light used by NLO-PDT allows for precise focusing of high intensity light within very small volumes leading to nonlinear effects through multiple photon interactions. NLO-PDT allows for the use of lower energy laser light in the near-infrared region that has deeper depth of tissue penetration to activate photosensitizing chemicals that are normally activated by short wavelength, higher energy light that can cause cellular damage and has short depth penetration into tissues. Photosensitizers such as riboflavin that are excited by ultraviolet light (UV) are currently being used to treat corneal thinning by inducing oxygen radical generation leading to collagen crosslinking (CXL) and corneal stiffening. Additionally UV-CXL has been used as an anti-microbial method to treat corneal infections and to inhibit corneal swelling in bullous keratopathy.

A major drawback of UV-CXL is that there is no control over the volume of tissue where free radicals are generated when conventional UV light is used. This can lead to unwanted effects including cellular damage below the region of cross linking that may involve the corneal endothelium which is a nonregenerative cell layer in the cornea that is responsible for maintaining corneal transparency and limits the volume available for crosslinking. Therefore, the purpose of using NLO photoactivation is to generate free radicals only in the focal volume of the laser beam where NLO effects occur. This volume can be precisely controlled by lenses/objectives used to focus the light into the tissue, thereby leading to highly localized photoactivation.

NLO-PDT will allow for precise depth and area activation of photosensitizers that conventional UV-CXL lacks. Generation of free radicals by NLO femtosecond lasers can also be used to kill cells, bacteria, tumors and neovascular vessels growing into the avascular cornea with more precision then current approaches. The advantage of the disclosed NLO-PDT methodology is that activation of photosensitizer will occur only at the focal plane defined by the focusing objective of the laser. This will allow precise localization of oxygen radical generation and corneal crosslinking and anti-microbial and tumorcidal activity, as well as crosslinking in deeper corneal layers without damaging the corneal endothelium.

There are at least four immediate uses for localized NLO-PDT. First, collagen crosslinking and corneal stiffening can be used to more precisely stiffen weakened corneas, such as keratoconus and post-LASIK ectasia. Currently UV crosslinking is used clinically to treat these diseases. The disclosed approach will replace the current standard of care. Second, since crosslinking results in corneal stiffening and compensatory flattening and steepening in different regions, the disclosed NLO-PDT method can be used to precisely stiffen, flatten and steepen regions of the cornea to treat astigmatism and refractive errors associated with myopia, hyperopia and presbyopia. Third, the disclosed NLO-PDT methodology can be used to treat bacterial, fungal, and amoebic infections of the eye without antibiotics. Generation of free radicals is already used to sterilize tissue and fluids. NLO-PDT based oxygen radical generation can be used in a similar therapeutic modality with the disclosed methodology. Fourth, the disclosed NLO-PDT methodology can be used to kill labeled tumor cells in the eye following loading with photosensitizing dyes. The disclosed NLO-PDT methodology can be used to treat a range of clinical diseases including keratoconus, post-LASIK ectasia, astigmatism, myopia, hyperopia, infection and ocular tumors.

FIG. 1 is a simplified block diagram of an apparatus 10 implementing one embodiment of the invention. Femtosecond infrared pulsed laser 12 has a tunable output 14 from 700 to 960 nm that is scanned by an x/y scan unit 16 through a beam expander (lenses 18 and 20) and focusing optics 22 into a cornea 24. For experimental purposes the focusing optics is a conventional objective able to selectively focus the pulsed light into a volume of 22 $\mu m^3$ located at 5.5 mm below the objective tip. Depth and volume of focus can be selectively manipulated by modification and movement of the focusing optics 22.

Two-photon excited fluorescence (TPEF) occurs when a fluorophore absorbs two or more photons of near-infrared light (700 to 960 nm) and emits a visible light photon. Two-photon excited fluorescence differs from single photon excited fluorescence (SPEF) in that the two-photon excited fluorescence signal is generated only at the focal plane, is less phototoxic than single-photon excited fluorescence, exhibits dramatically improved axial resolution and has a deeper depth of tissue penetration.

In an experiment illustrating the disclosed embodiment, fresh enucleated rabbit eyes were treated with 0.1% riboflavin in a 20% dextran solution by volume for 30 minutes. The eyes were moved relative to the objective 22 using an x-y translational stage with lateral movement of 10 mm/sec with a 3 µm line separation. The central cornea region was exposed to 760 nm Chameleon femtosecond laser light at 190 mW using laser 12 and a 20× objective 22. The axial position of the beam focus was controlled by moving the eye relative to the fixed focal plane defined by objective 22. The corneas were then removed, fixed and evaluated for TPEF collagen autofluorescence, which was measured using a Zeiss multiphoton confocal microscope.

Figure 2A:
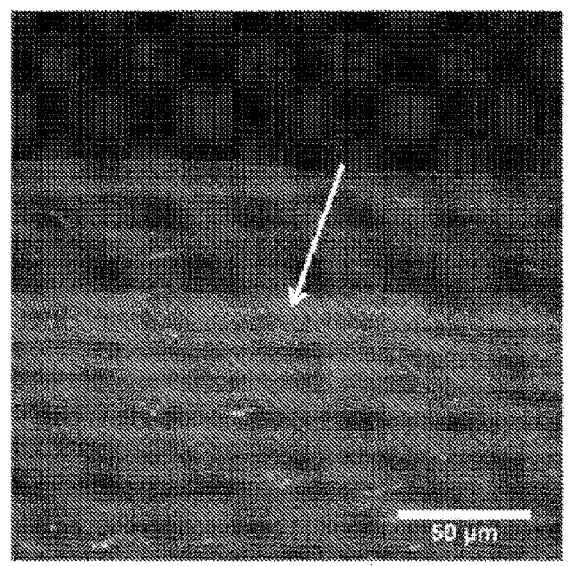
FIG. 2a is a side cross-sectional view of a microphotograph of an NLO treated rabbit cornea.

Multiphoton excitation of riboflavin within the corneal stroma generated fluorescence and free radicals leading to collagen crosslinking. NLO-PDCx1 induced collagen autofluorescence within 91 mm line scans with 3 .mu.m line separation is shown in the TPEF image shown in FIG. 2a.

Figure 2B:
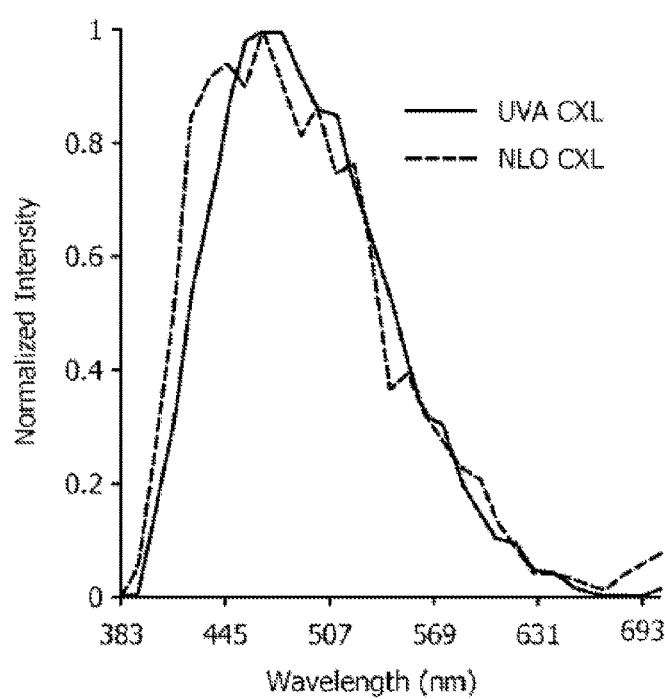
FIG. 2b is a comparative graph of the autofluorescence of a UVA and an NLO treated rabbit cornea.

The NLO-PDCx1 autofluorescence spectrum is shown graphically in FIG. 2b and compared against UVA collagen crosslinking autofluorescence in the cornea after 30 minutes irradiation in FIG. 2b. The normalized collagen autofluorescence spectrum generated by NLO-PDCx1 as shown in FIG. 2b is very similar to the autofluorescence spectrum generated by UVA crosslinking. Therefore, selectively focused femtosecond laser beams can be used to create collagen crosslinking and corneal stiffening with similar biological effects as are observed with the more uncontrolled UVA induced crosslinking of the prior art.

In another demonstration of the concept of the invention collagen hydrogels were made and their mechanical stiffening using the methodology of the invention was measured. Compressed collagen hydrogels were made by polymerizing 3 ml of rat-tail type-1 collagen gel (3 mg/ml) in a 24 well tissue culture plate. Gels were compressed to 100 .mu.m thickness using conventional methods. To facilitate transport, gels were compressed onto #54 Whatman Filter discs having a central 7.6 mm diameter hole exposing the hydrogel for biomechanical testing and NLO CXL.

Figure 3A:
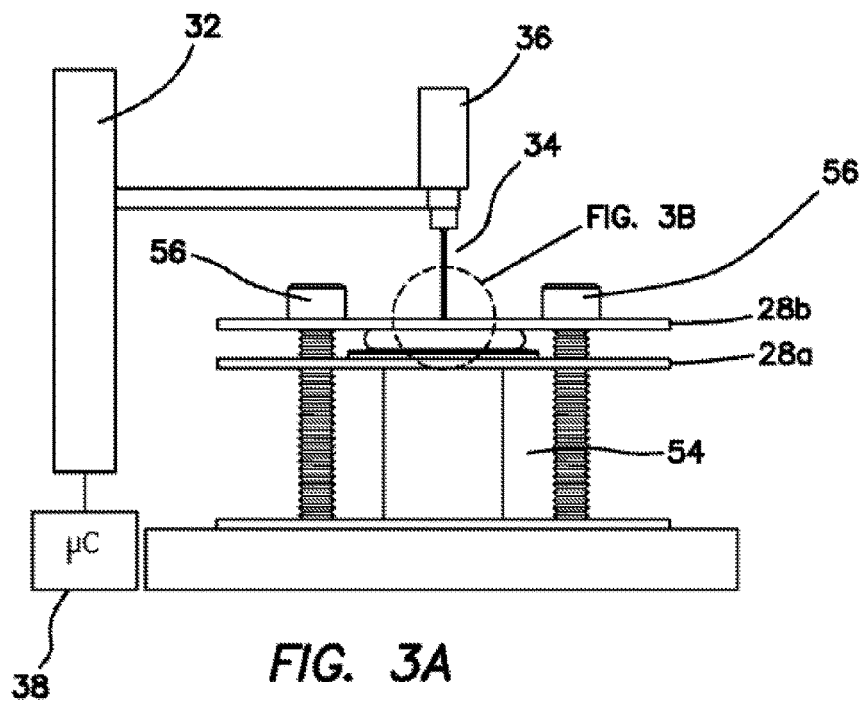
FIGS. 3a and 3b are a side cross-sectional view and a cutaway perspective view respectively of a jig where in the elasticity of gels subject to the method of the invention are measured.
Figure 3B:
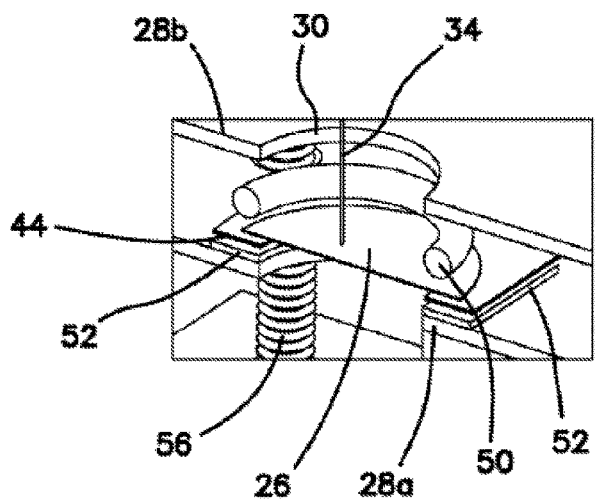

As shown in FIGS. 3a and 3b a jig was made to measure the elastic modulus of the gels 26, which were clamped between two steel plates 28a and 28b, each having a 7.6 mm diameter central hole 30 on a three dimensional control assembly 32. Plate 28a is mounted on a hollow transparent cylinder 54. Gel 26 is mounted on filter paper 44 and gasket 52 on top of plate 28a, each including a central hole 30 as best shown in FIG. 3b. An O-ring 50 is mounted on top of gel 26 followed by plate 38b. Plates 28a and 28b are bound together by compression from bolts 56. Gels 26 were then indented using a 250 μm diameter round tipped probe 34, as shown in FIG. 3b, attached to a force transducer 36 driven by automated electrical step motor within control assembly 32 controlled and recorded by computer 38 as shown in FIG. 3a. Each gel 26 was indented at the center through 1 mm depth at the velocity of 20 μm/sec and indenting force and depth recorded every 0.05 sec through 10 cycles. The elastic modulus, E, was then calculated using Equation 1, which is the modified Schwerin point-load solution of elastic modulus.

$$E = \frac{(f(v))^3 a^2 P}{\delta^3 h}$$

$$f(v) \approx 1.049 - 0.146v - 0.158v^2$$

Where P is the indenting force, a the radius of hole 30, h the gel thickness, v the Poisson ratio, and δ the indenting depth.

Figure 5:
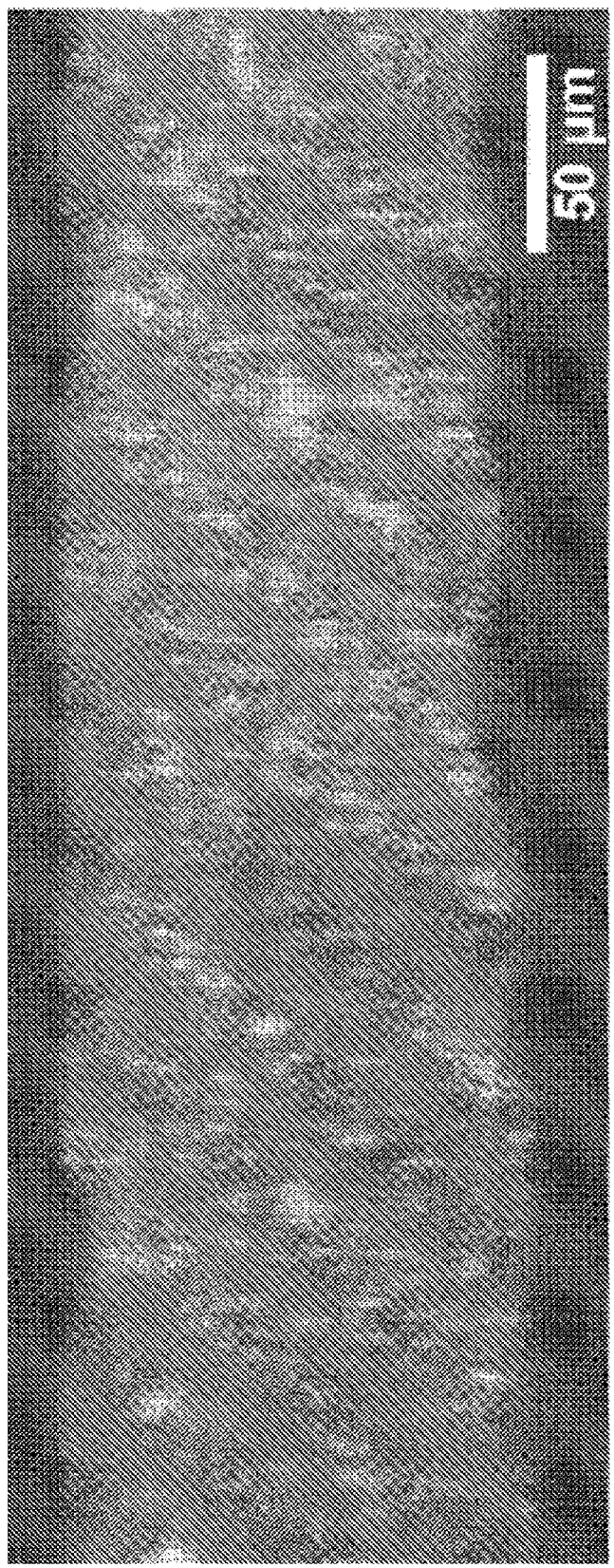
FIG. 5 is a data scan of a gel using second harmonic generation to determine its thickness.

Gels 26 were then soaked in 0.1% riboflavin in phosphate buffered saline (PBS) and mounted in an NLO crosslinking chamber 40 as shown in FIG. 4a. The chambers 40 were then mounted onto a Zeiss 510 Meta confocal laser scanning microscope (CLSM) and gel thickness measured by second harmonic generation (SHG) imaging as shown in FIG. 5. NLO CXL was then performed by focusing a 100 mW (NLO I) or a 150 mW (NLO II), 760 nm femtosecond laser beam into the gel 26 using a 20× Zeiss apochromat objective lens 22 (NA=0.75). Gels 26 were scanned at 27.8 cm/sec velocity over a 5.2 mm×5.2 mm square area through the gel at 2 μm steps in a three dimensional tile scan as shown in FIGS. 4b and 4c. Control and UVA CXL gels 26 were left in the chamber 40 for the same duration as NLO CXL. For UVA CXL gels 26 were removed from the chamber 40 and exposed to 370 nm UVA light at 3 mW/cm² for 30 min over the same area as NLO CXL. The indenting force was then re-measured for each gel 26 as well as gel thickness.

Figure 6:
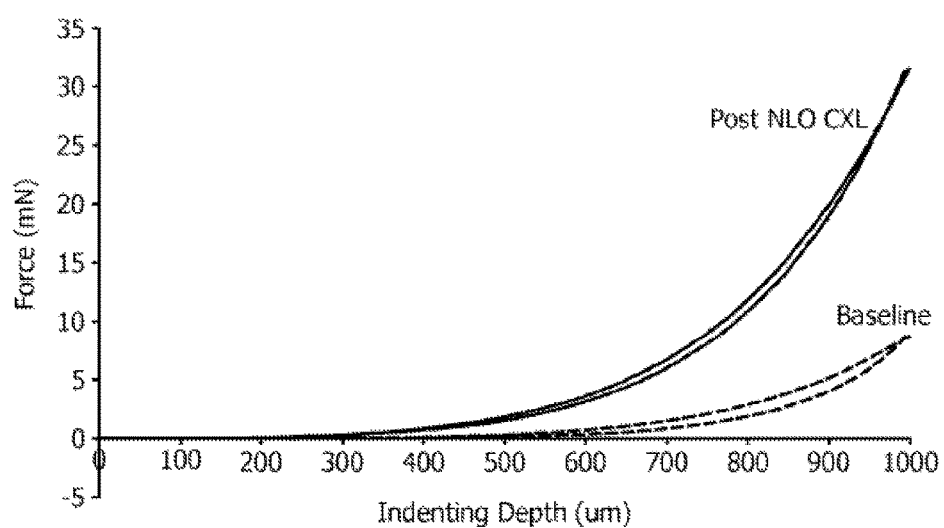
FIG. 6 is a graph of the indenting force verses the indenting depth for the gels before and after irradiation according to the methodology of the invention.
Figure 7:
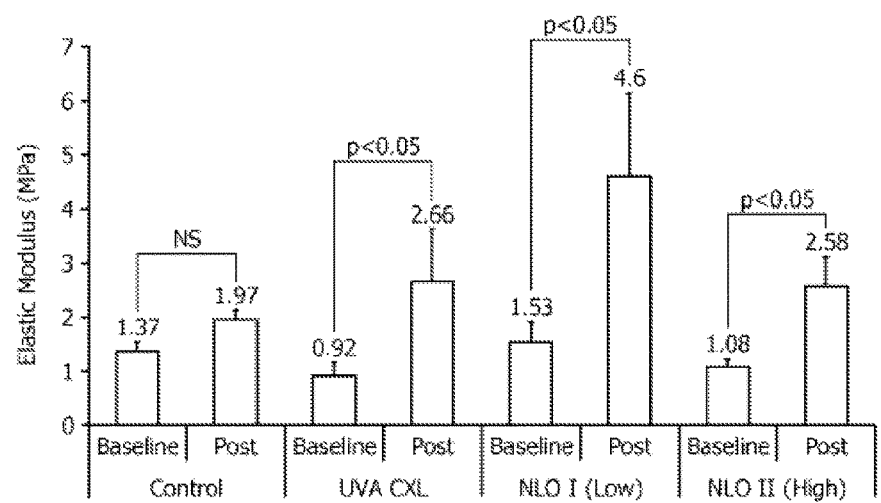
FIG. 7 is a graph of the elastic modulus of the gels comprised of a control group, a UVA exposed gel, a low power (100 mW) nonlinear optic (NLO) exposed gel and a high power (150 mW) nonlinear optic (NLO) exposed gel.
Figure 8:
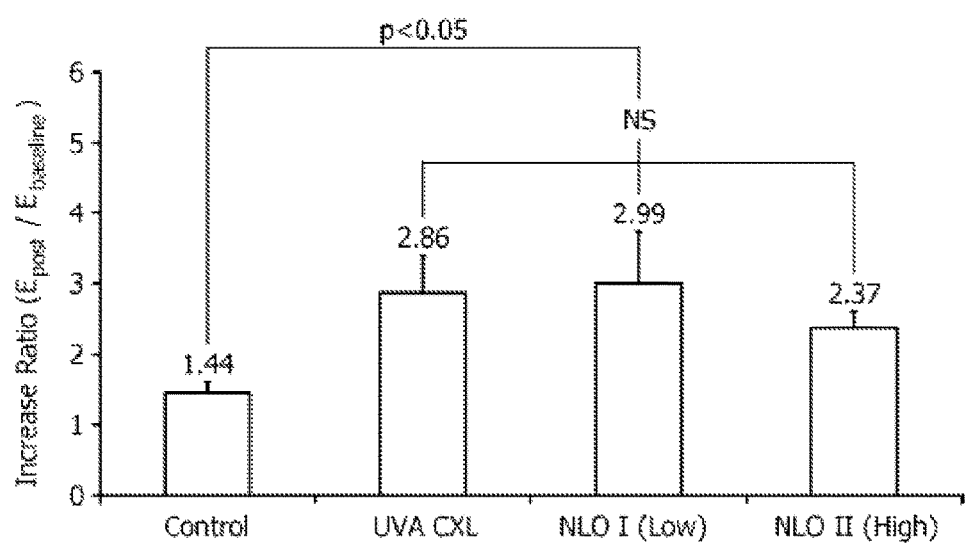
FIG. 8 is a graph of the increase in ratio of post to baseline elasticity of the treated gels comprised of a control group, a UVA exposed gel, a low power (100 mW) nonlinear optical (NLO) exposed gel and a high power (150 mW) nonlinear optical (NLO) exposed gel.

NLO collagen hydrogel crosslinking is shown in FIG. 6 at the $10^{th}$ cycle. NLO I treatment resulted in a marked increase in the indenting force suggesting that CXL and stiffening were induced by NLO I treatment. FIG. 7 shows baseline and post-treatment E values for each group before and after. Significantly increased post-treatment E values (p<0.05) were observed for all of CXL treatment groups. No significant difference was detected in the control group (p=0.22). Comparison of the ratio in E values between pre and post CXL (FIG. 8) showed no significant difference between UVA CXL and NLO CXL (p=0.38);

We thus show that nonlinear optical, multiphoton excitation of riboflavin using a femtosecond laser can induce collagen hydrogel crosslinking and mechanical stiffening similar to UVA CXL. Increased collagen autofluorescence in the cornea suggests that NLO CXL can stiffen the cornea. Because of the higher axial resolution of multiphoton processes, NLO CXL provides a safer and more effective therapeutic approach to treating corneal ectasia.

Ultraviolet A (UVA) mediated corneal crosslinking (UVA-CXL) is a known method to stiffen corneas, originally developed as a treatment for keratoconus (KC). Stiffening is achieved by using UV light to activate a photosensitizer such as riboflavin, which leads to the formation of free radicals that in turn causes the formation of additional crosslinks. Traditionally, the UV light is emitted by diodes used to effectively expose the entire cornea at one time.

Figure 9:
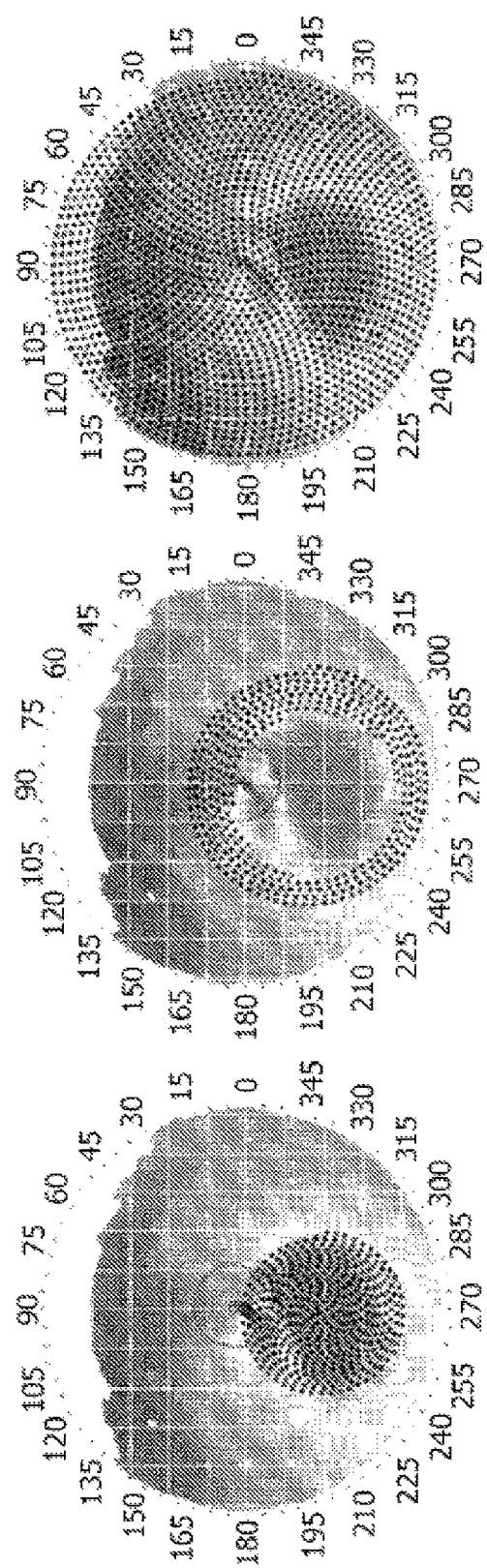
FIGS. 9a-9c illustrate three possible crosslinking patterns in the corneal tissue among an unlimited number of possibilities with the present invention.

Two-photon corneal crosslinking (2P-CXL) uses an alternate approach to activate the photosensitizer. Here, ultrashort (femtosecond-range) infrared laser pulses are focused into the tissue. In the focal spot 25, which is typically only a few femtoliters in volume, two infrared photons interact to form a single UV photon, which then performs the photoactivation. This process is limited to a very small focal volume, and thus allows for very precise positional control of crosslinking. In addition to being able to crosslink only parts of the cornea as shown in FIG. 9a, it is possible to create almost any conceivable pattern as shown in the example of FIG. 19b. 2P-CXL further expands the capabilities of CXL by allowing crosslinking of the deeper layers of the cornea, which is not possible using the conventional approach. Using conventional UV diodes, only the anterior portion of the cornea can be crosslinked so as to avoid damaging the corneal endothelium, the deepest layer of the cornea. Without the endothelium, the cornea cannot function. Because the CXL volume is very limited in 2P-CXL, crosslinking can be performed close to the endothelium without risking damage.

However, the small focal volume is also the main drawback of 2P-CXL. Since only a small portion of the cornea is being crosslinked at a time, two photon crosslinking is a process which is very slow. Conventional UVA-CXL has an exposure time of 30 minutes. Research is currently ongoing to reduce that time to 10 minutes or less. By contrast, using a small, micron-sized focal volume as contemplated here, crosslinking a similar corneal volume would take up to 8 hours. This is dearly beyond a reasonable clinical time span during which it can be practically used as a therapeutic method. It is preferable that therapeutic procedures be completed within short patient exposure times of the order of tens of minutes or less than 10 minutes in order for the treatment duration to be clinically accepted. In the preferred embodiment a clinical exposure of cross-linking the entire cornea is approximately 5 minutes or less in duration is the acceptable clinically accepted time.

To address this problem, there are two possible approaches:

a. Increase the scanning speed by moving the focal spot more rapidly across the cornea. While feasible from a mechanical standpoint, it would also require significantly higher energies in order to activate the photosensitizer. To achieve measurable crosslinking, power levels that far exceed the FDA-allowed limits would have to be employed. A safe intensity of the laser light is understood to be equal to or less than the FDA maximum allowed limit for laser exposures, which may be dependant on the kind of tissue irradiated and the wavelength of the light. Currently, the FDA has set a safe maximum limit on femtosecond lasers of 1 watt of delivered power. It must be understood that the safe maximum limit may be varied by the FDA over time and may depend on the nature or modulation of the laser and pulse or irradiation delivered. A variation of this proposed approach is illustrated by Lubatschowski's multifocal approach disclosed in US Patent Pub. US 2007/0123845, which proposes splitting up the beam and using more than one focal spot simultaneously. Setting the engineering obstacles to this approach aside, because the beam is split into several spots, the unsplit original beam would have to be several times more powerful than the safe intensity. The resulting power levels of the originating beam would be markedly higher than allowed by FDA safety regulations.

b. Expand the focal spot size, thereby crosslinking larger volumes at the same time so that the selected volume of the tissue to be treated can be scanned more quickly. Essentially, this is a hybrid approach sacrificing some positional accuracy for much higher scanning speeds.

The disclosed device uses a single, low numerical aperture (NA) lens. The lower the NA, the larger the focal volume. The NA of a lens is dependent on its focal length, which is a fixed parameter, and on the diameter of the incoming beam. Essentially, in order for the lens to achieve its maximum possible NA and therefore its smallest focal spot size, the beam has to completely fill or even overfill the back aperture of the lens. The beam diameter is inversely proportional to the focal volume with all other parameters kept constant. By making the beam diameter smaller than the lens diameter, the lens becomes "less effective". Therefore, by varying the diameter of the laser beam, we can vary the effective NA of the lens, and thereby vary the focal spot volume.

Figure 10:
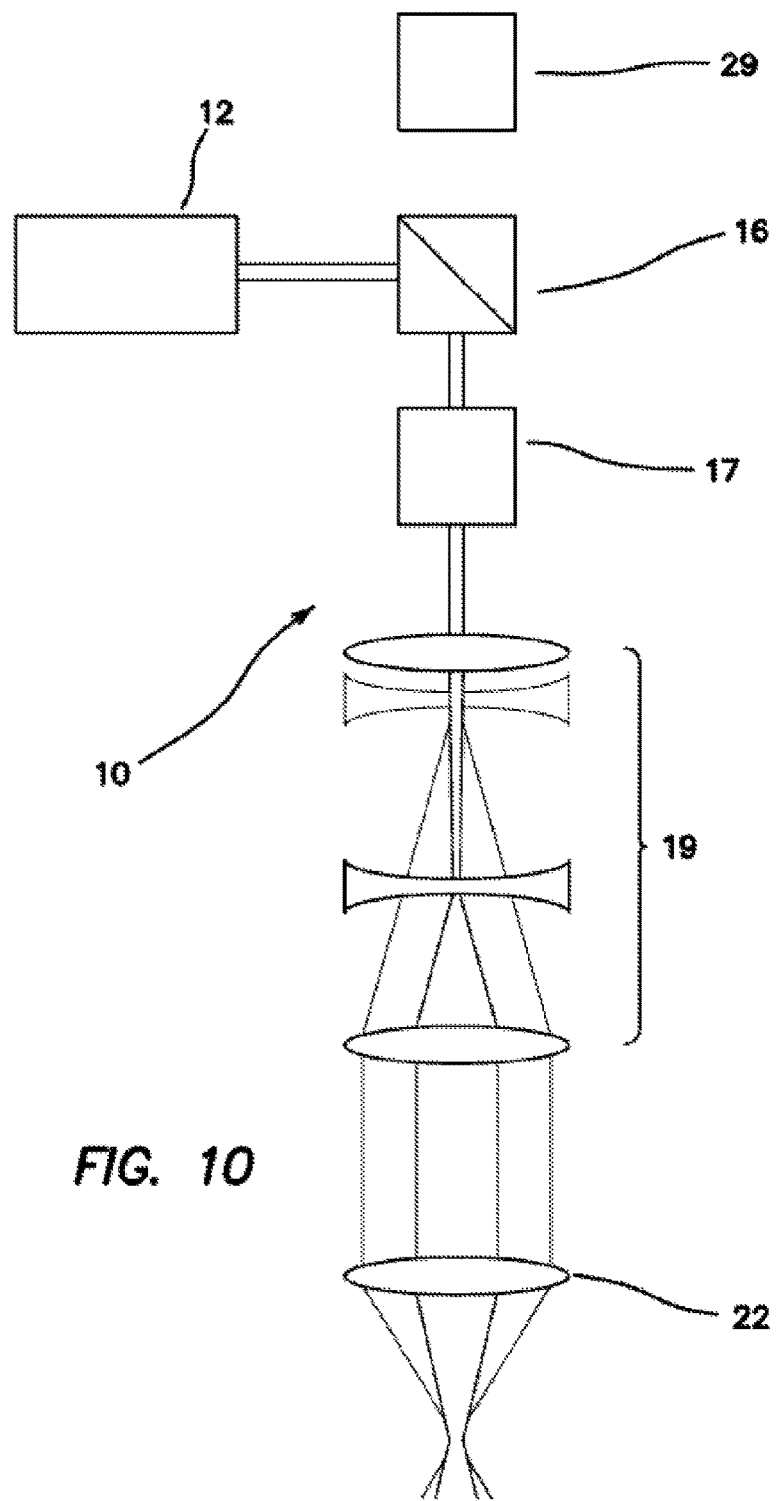
FIG. 10 is a schematic representation of the optics of another embodiment of device.

FIG. 10 is a schematic representation of the optics of another embodiment of device 10. Infrared laser pulses are generated by the femtosecond laser 12 and sent through a dichroic beam splitter 16. The beam splitter "sorts" light by wavelength in that it reflects certain wavelengths, in this case infrared light, while letting others pass through. Being infrared, the laser beam is reflected into the X/Y scan unit 17. This unit is comprised of two or more computer-controlled mirrors that can move the beam in x and y directions or in a plane perpendicular to the depiction of FIG. 10. The scanned beam then enters a variable beam expander 19. Essentially a variable-zoom telescope, this computer-controlled expander 19 allows us to adjust the beam diameter. The adjusted beam is then focused into the tissue by a focal or focusing lens 22, the effective NA of which is controlled by the beam diameter. In the illustrated embodiment part of multiphoton UV light created in the focal spot 25 is relayed back through the optical system and, due to its lower wavelength, passes through the beam splitter 16 into a spectral analyzer 29 which is used to monitor the procedure. A clinical embodiment of the device 10 might include the analyzer 29 as an option.

Figure 11:
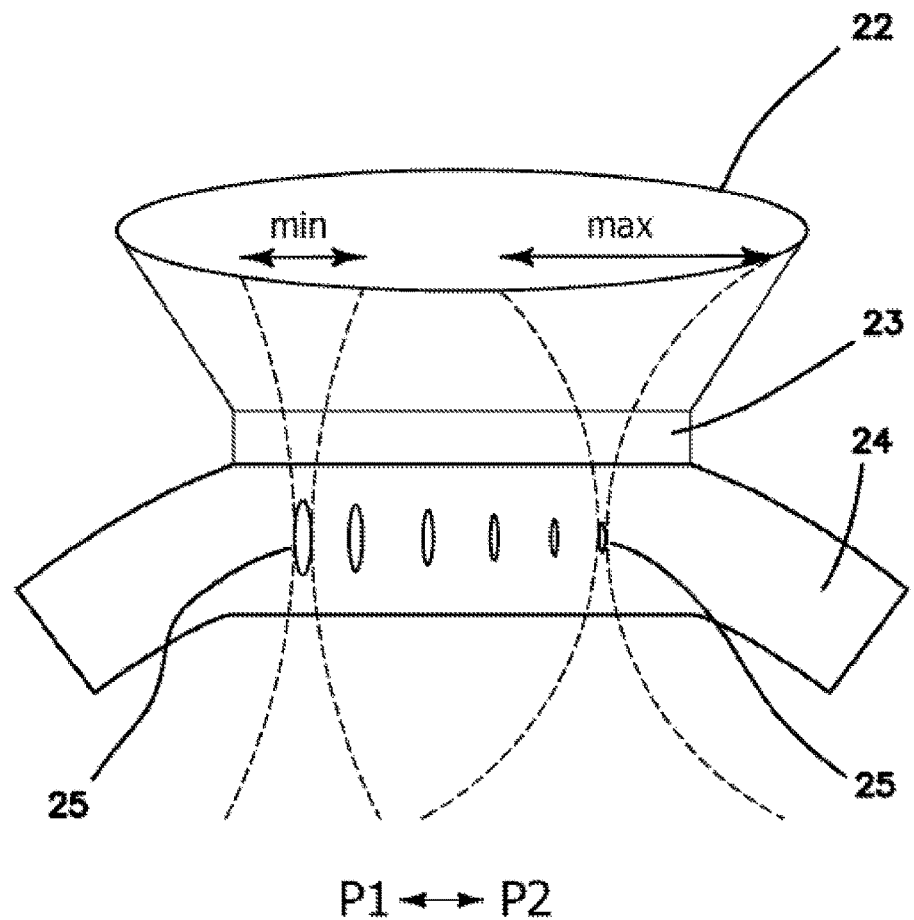
FIG. 11 is a diagram of the effects in the corneal tissue of varying the beam diameter.

The effects of varying the beam diameter are shown in FIG. 11. To ensure a smooth, even optical surface of the cornea 24, a single-use applanation cone 23 is used to applanate or flatten the central cornea 24 and to optically couple the patient's eye to device 10. At its minimum setting, the beam has a diameter significantly smaller than that of the focusing lens 22, resulting in a large focal volume P1 shown in the left of FIG. 12. By increasing the diameter, the focal volume is decreased, until the beam diameter is greater than the diameter of the focusing lens, allowing the lens to act at maximum efficiency and resulting in a very small focal volume P2 shown in the right of FIG. 12 as a comparative example. We can therefore choose between speed and precision as necessary. The larger the focal volume the faster that a selected volume of the cornea 24 can be scanned. Conversely, the smaller the focal volume the slower that a selected volume of the cornea 24 can be scanned. Scanning speed and focal volume are selected to achieve clinically acceptable exposure times of a selected volume of cornea 24 using a pulsed laser light at safe intensities to effectively activate the photosensitizer. The correct selection of parameters can be determined empirically in each case or by calculation using first principles of the photomediation of tissue.

Figure 12:
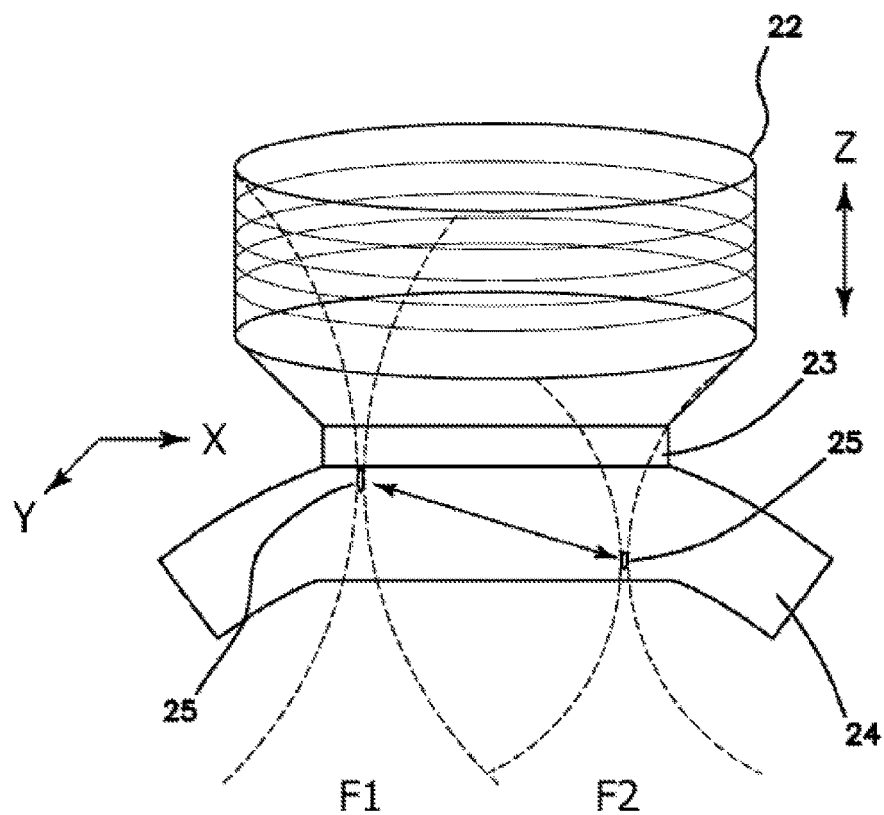
FIG. 12 is a diagram of the effects in the corneal tissue of varying the relative position of the focusing lens to the applantion cone or cornea.

In the depiction of FIG. 12, the z-direction is vertical on the plane of the drawings, the x-direction is to the left in the plane of the drawing and the y direction is perpendicular to the plane of the drawing. The focal spot 25 can be precisely positioned and moved in three dimensions. Its x, y position of the focal spot 25 relative to applanation cone 23 and hence cornea 24 is controlled by the x/y scan unit 17. To control its z position in the tissue or depth in the tissue, the focusing lens 22 is moved in the z-direction relative to the applanation cone 23 and thus relative to the cornea tissue 24 between the position shown in the left of FIG. 12 as F1 and on the right of FIG. 12 as F2. In the diagram of FIG. 12, focusing lens 22 is shown in multiple positions, with the resulting location of the focal spot 25 in corneal tissue 24 being shown only in the two extremums of the corneal positions corresponding to the extremum positions of focusing lens 22. Any vertical position between the corneal extremums can be chosen by positioning lens 22 in a corresponding relative z-displacement with respect to the applanation cone 23. The z-displacement of lens 22 is coordinated by computer with the x,y scanning of scan unit 17 to provide the desired coverage of the selected volume of the tissue. Thus, not only is the absolute magnitude of the volume selected, but also its three dimensional location in the tissue.

The three dimensional movement of a variable volume focal spot 25 allows us to create almost arbitrary crosslinking patterns in the tissue with clinically acceptable exposure times and safe levels of laser exposure. FIGS. 9a-9c show examples of possible patterns mapped onto a surface topography map of a keratoconus cornea 24. In addition to following the conventional protocol for KC crosslinking by exposing the entire cornea as shown in FIG. 9c, we can limit crosslinking to just the cone area as shown in FIG. 9a or create a stabilizing annulus by crosslinking the area around the cone as shown in FIG. 9b.

Lubatschowski's device uses a 0.3 NA lens, which gives a theoretical two photon volume of less than 19 femtoliters. The variable or effective NA methodology and apparatus disclosed here allows us to vary the NA between 0.16 and 0.08 with corresponding focal volumes between 150 and 2500 femtoliters. At its maximum setting, this gives a focal volume 130 times greater than that of the 0.3 NA lens. To achieve similar speeds, a multifocal method and apparatus as disclosed by Lubatschowski with a 0.3 NA lens would have to provide an array of at least 11 by 11 or 121 separate spots of laser light to achieve the same effect with a corresponding increase of intensity of the originating or unsplit laser beam. The NA values of 0.16/0.08 and the corresponding focal volumes disclosed above are based on the illustrated embodiment. However it must be understood that these values are by no means the absolute theoretical limits of a variable NA beam delivery system according to the present scope of the invention. By using a different focal lens 22 with a larger diameter and different focal length, for example, it is possible to increase the range of focal volumes further consistent with the teachings and scope of the invention.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

What is claimed is:

1. A method of nonlinear optical photodynamic therapy of a cornea, the method comprising:
    pretreating the cornea with a photosensitive agent, which is capable of generating free radicals within a treatment volume of the cornea upon laser irradiation; and providing the photodynamic therapy within the treatment volume of the cornea by:
    directing to said cornea laser irradiation by a pulsed near-infrared laser light, which provides a multiphoton beam at a predetermined intensity and having a near-infrared wavelength through a focusing objective lens of an apparatus, the multiphoton beam having a beam width and the focusing objective lens having a fixed numerical aperture;
    generating a focal volume with the multiphoton beam at a depth in the cornea by reducing an effective numerical aperture of the apparatus, compared to the numerical aperture of the focusing objective lens, to a final value between 0.16 and 0.08 by expanding the beam width impinging on the focusing objective lens, wherein the focal volume comprises is between 150 and 2500 femtoliters; and
    moving the focal volume in three dimensions relative to the tissue within a predetermined clinical time span, to define the treatment volume, which is larger than the focal volume.

2. The method of claim 1, wherein the photosensitive agent comprises riboflavin.

3. The method of claim 1, wherein the wavelength is 700-960 nm.

4. The method of claim 1, wherein the pulsed near infrared laser light within the cornea provides an intensity and length of irradiation to cause collagen crosslinking (CXL).

5. The method of claim 1, wherein the pulsed near infrared laser light within the cornea provides an intensity and length of irradiation that provides anti-microbial mediation.

6. The method of claim 1, wherein the pulsed near-infrared laser light within the cornea provides an intensity and length of irradiation that inhibits corneal swelling in bullous keratopathy.

7. The method of claim 1, wherein the pulsed near-infrared laser light within the cornea provides an intensity and length of irradiation that kills cells, bacteria, tumors or neovascular vessels growing into the cornea.

8. The method of claim 1 comprising activating the photosensitizing agent only at a focal plane of the focal volume by limiting intensity and length of irradiation by the pulsed near-infrared laser light within the cornea.

9. The method of claim 1 comprising crosslinking collagen in the cornea by an intensity and length of irradiation by the pulsed near-infrared laser light to precisely stiffen the cornea, wherein the cornea is initially weakened prior to being stiffened.

10. The method of claim 1 comprising adjusting the pulsed near-infrared laser light within the cornea to provide an intensity and length of irradiation that causes corneal stiffening, flattening and steepening to precisely stiffen, flatten and steepen regions of the cornea, thereby treating an astigmatism or a refractive error associated with myopia, hyperopia or presbyopia.

11. The method of claim 1, wherein the pulsed near infrared laser light within the cornea provides an intensity and length of irradiation that treats bacterial, fungal, or amoebic infections of the cornea without antibiotics.

12. The method of claim 1, wherein the pulsed near-infrared laser light within the cornea provides an intensity and length of irradiation that kills labeled tumor cells in the cornea following loading with photosensitizing dyes.

13. The method of claim 1, comprising adjusting an intensity and length of irradiation of the pulsed near-infrared laser light within the cornea to treat a clinical disease.

14. The method of claim 9 comprising treating a keratoconus or a post-LASIK ectasia.

15. The method according to claim 13, wherein the clinical disease is selected from the group consisting of keratoconus, post-LASIK ectasia, astigmatism, myopia, hyperopia, presbyopia, infection and an ocular tumor.

* * * * *